(12) United States Patent
Zanker et al.

(10) Patent No.: US 7,373,808 B2
(45) Date of Patent: May 20, 2008

(54) METHOD AND ULTRASONIC METER SYSTEM FOR DETERMINING PIPE ROUGHNESS

(75) Inventors: Klaus J Zanker, Houston, TX (US); John R Lansing, Houston, TX (US)

(73) Assignee: Daniel Measurement and Control, Inc., Houston, TX (US)

( * ) Notice: Subject to any disclaimer, the term of this patent is extended or adjusted under 35 U.S.C. 154(b) by 0 days.

(21) Appl. No.: 11/382,160

(22) Filed: May 8, 2006

(65) Prior Publication Data

US 2006/0272417 A1 Dec. 7, 2006

Related U.S. Application Data

(60) Provisional application No. 60/686,249, filed on Jun. 1, 2005.

(51) Int. Cl.
*G01B 5/28* (2006.01)
(52) U.S. Cl. .......................................... 73/105; 73/597
(58) Field of Classification Search .................. 73/592
See application file for complete search history.

(56) References Cited

U.S. PATENT DOCUMENTS

| | | | | |
|---|---|---|---|---|
| 4,300,401 A | * | 11/1981 | Pedersen | 73/861.31 |
| 6,047,602 A | * | 4/2000 | Lynnworth | 73/632 |
| 6,067,861 A | * | 5/2000 | Shekarriz et al. | 73/861.25 |
| 2003/0101804 A1 | * | 6/2003 | Zanker | 73/105 |
| 2005/0055171 A1 | * | 3/2005 | Freund et al. | 702/89 |

OTHER PUBLICATIONS

Klaus J. Zanker, "Diagnostic Ability of the Daniel Four-Path Ultransonic Flow Meter," Article Published at WWW.EMERSONPROCESS.COM Website at Least as Early as the Filing Date of U.S. Appl. No. 11/382,160.

* cited by examiner

*Primary Examiner*—Hezron Williams
*Assistant Examiner*—Rose M Miller
(74) *Attorney, Agent, or Firm*—Mark E. Scott; Conley Rose, P.C.

(57) ABSTRACT

A method and ultrasonic meter system for determining pipe roughness. At least some of the illustrative embodiments are ultrasonic meters comprising a spool piece that couples within a flow of fluids, and a first transducer pair mechanically mounted to the spool piece and acoustically coupled to the flow of fluids (wherein the first transducer pair comprises an upstream transducer and a downstream transducer in operational relationship to the upstream transducer and defines a first chord there between). The ultrasonic meter is configured to determine diagnostic data based on acoustic signals transmitted between the first transducer pair (wherein the diagnostic data comprises an asymmetry of the flow of fluids in the spool piece, a cross flow of the flow of fluids in the spool piece, and a profile factor of the flow of fluids in the spool piece). The ultrasonic meter is configured to determine changes in the roughness of a pipe mechanically coupled to the ultrasonic meter based on a trend of the diagnostic data (wherein the trend comprises a substantially constant value of about unity for both the asymmetry and the cross flow and a substantially changing value for the profile factor).

20 Claims, 6 Drawing Sheets

FIG.3
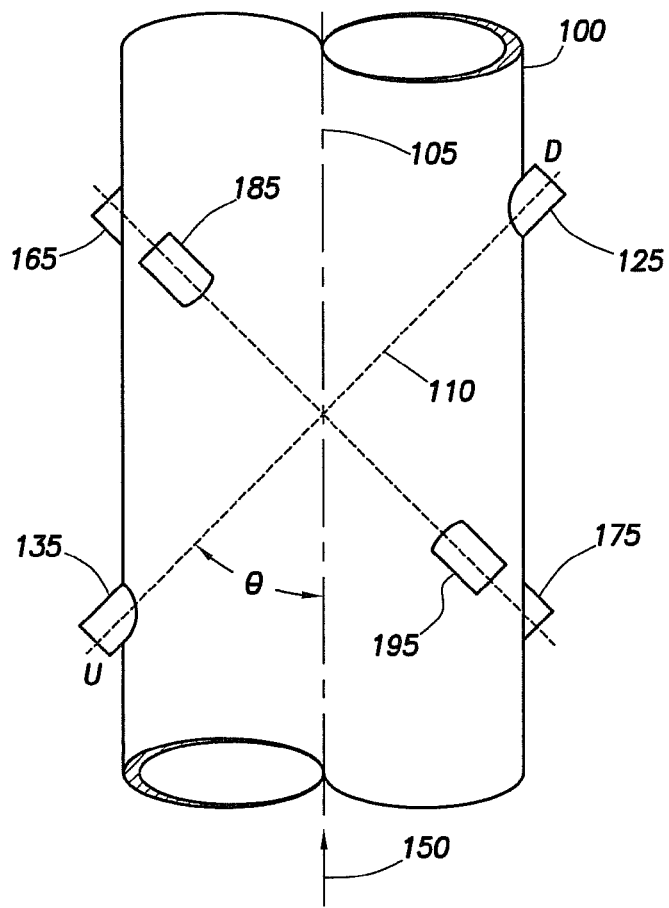
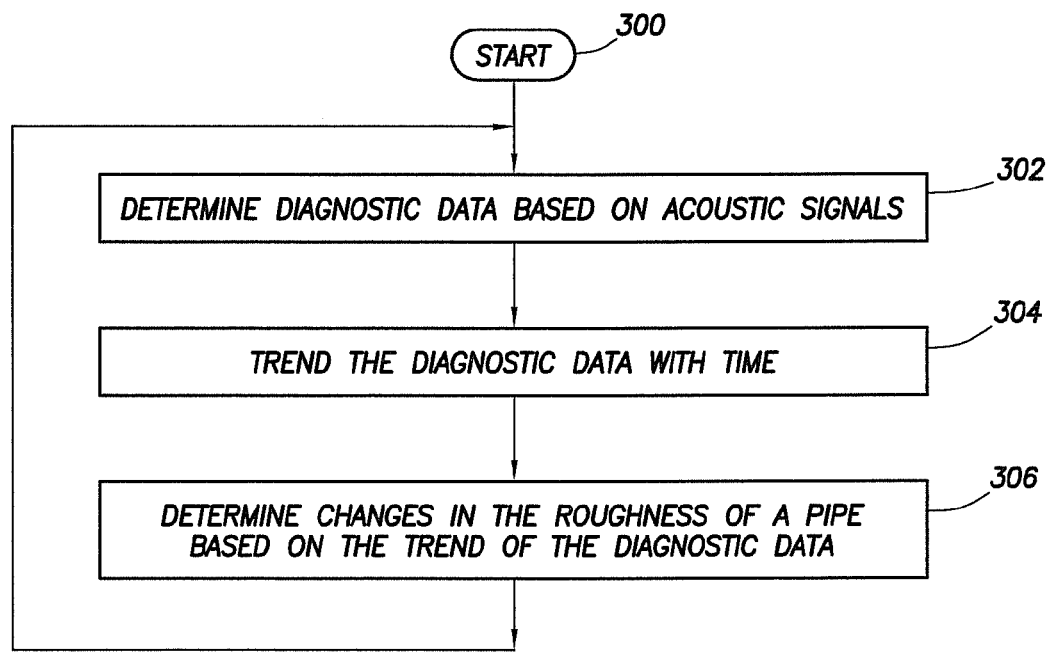
FIG.8

METHOD AND ULTRASONIC METER SYSTEM FOR DETERMINING PIPE ROUGHNESS

CROSS-REFERENCE TO RELATED APPLICATIONS

This application claims the benefit of Provisional Patent Application Ser. No. 60/686,249, titled "Ultrasonic meter diagnostics to recognize pipe roughness," filed Jun. 1, 2005, and which is incorporated by reference herein as if reproduced in full below.

BACKGROUND

Measurements of mass and volume flow rates of fluid through a conduit are a part of operations in the oil and gas industry. One of the tools used to accomplish such a measurement is an ultrasonic flow meter. Ultrasonic flow meters are a class of flow meters that determine volumetric flow of a fluid within a conduit using ultrasonic signals propagated through the fluid.

Ultrasonic flow meters offer an advantage of generating an abundance of diagnostic data that may reveal potential problems in the performance of the meter. However, shifts in the diagnostic data have been difficult to interpret because the data is most often reviewed after either new meter calibration or field failures of the meter. Industry practice calls for fixed routine maintenance and mandatory recalibration intervals of flow meters. Such a maintenance and recalibration schedule may be expensive and time-consuming. Furthermore, if it is performed on a fixed interval, it is uncertain whether the meter actually requires such work to be performed. Thus, the abundance of diagnostic data provided by the flow meter is not being used efficiently.

There has been some practice of trending a limited quantity of diagnostic parameters with time in order to glean additional information. However, current methodologies are incomplete and lack optimization. These methodologies fall short of providing data significant enough to curb the need for fixed maintenance and calibration intervals. Additionally, current methods are not able to predict system performance beyond the flow meter such as an upstream pipe condition.

SUMMARY

The problems noted above are solved in large part by a method and ultrasonic meter system for determining pipe roughness. At least some of the illustrative embodiments are ultrasonic meters comprising a spool piece that couples within a flow of fluids, and a first transducer pair mechanically mounted to the spool piece and acoustically coupled to the flow of fluids (wherein the first transducer pair comprises an upstream transducer and a downstream transducer in operational relationship to the upstream transducer and defines a first chord there between). The ultrasonic meter is configured to determine diagnostic data based on acoustic signals transmitted between the first transducer pair (wherein the diagnostic data comprises an asymmetry of the flow of fluids in the spool piece, a cross flow of the flow of fluids in the spool piece, and a profile factor of the flow of fluids in the spool piece). The ultrasonic meter is configured to determine changes in the roughness of a pipe mechanically coupled to the ultrasonic meter based on a trend of the diagnostic data (wherein the trend comprises a substantially constant value of about unity for both the asymmetry and the cross flow and a substantially changing value for the profile factor).

Other illustrative embodiments are methods comprising determining diagnostic data based on acoustic signals transmitted between a first transducer pair of an ultrasonic meter (wherein the diagnostic data comprises an asymmetry of a flow of fluids that couples within a spool piece, a cross flow of the flow of fluids in the spool piece, and a profile factor of the flow of fluids in the spool piece), trending the diagnostic data with time, and determining changes in the roughness of a pipe based on the trend of the diagnostic data (wherein the trend comprises a substantially constant value of about unity for both the asymmetry and the cross flow and a substantially changing value for the profile factor).

Yet still other illustrative embodiments are computer-readable media comprising a plurality of instructions that, when executed by a processor, perform methods comprising determining changes in the roughness of a pipe based on a trend of diagnostic data with time (wherein the diagnostic data is based on acoustic signals transmitted between a first transducer pair and comprises: asymmetry of a flow of fluids that couples within a spool piece; cross flow of the flow of fluids in the spool piece; and profile factor of the flow of fluids in the spool piece). The trend comprises a substantially constant value of about unity for both the asymmetry and the cross flow and a substantially changing value for the profile factor.

The disclosed devices and methods comprise a combination of features and advantages which enable it to overcome the deficiencies of the prior art devices. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the various embodiments of the invention, reference will now be made to the accompanying drawings in which:

FIG. 3 illustrates a top view of an ultrasonic flow meter in accordance with embodiments of the invention comprising a spool piece housing transducer pairs;

FIG. 8 shows an exemplary flow diagram for determining pipe roughness.

NOTATION AND NOMENCLATURE

Certain terms are used throughout the following description and claims to refer to particular system components. This document does not intend to distinguish between components that differ in name but not function.

In the following discussion and in the claims, the term "comprises" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections. Further, the term "mounted" is intended to mean either an indirect or direct connection. Thus, if a first device is mounted to a second device, that connection may be through a direct connection, or through an indirect connection via other devices and connections.

DETAILED DESCRIPTION

Figure 1:
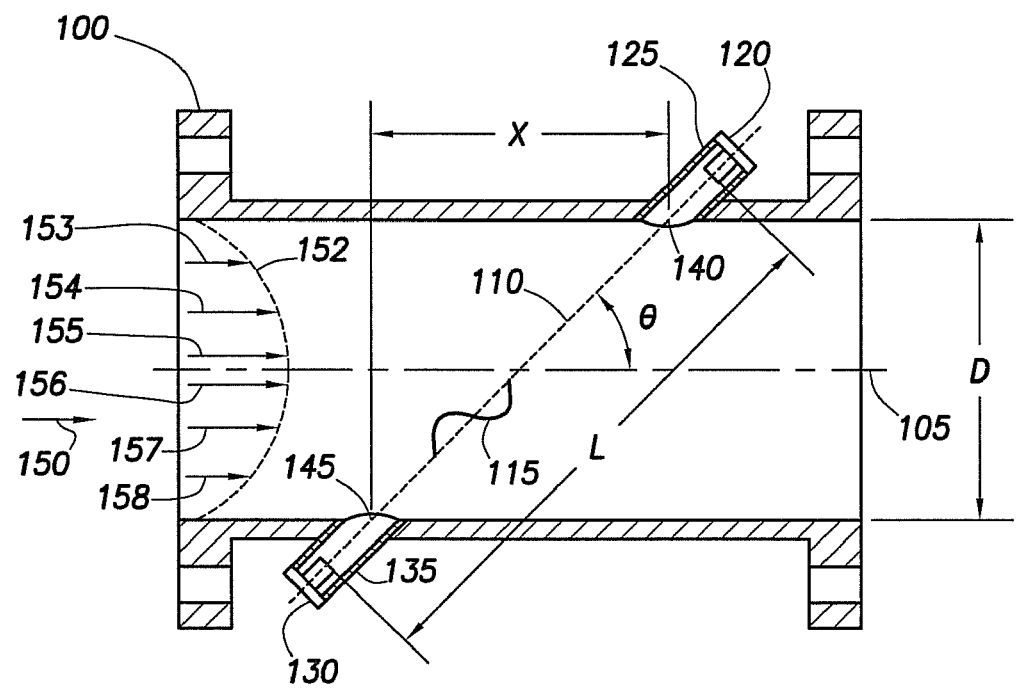
FIG. 1 illustrates a cut-away top view of an ultrasonic gas flow meter.

FIG. 1 illustrates an ultrasonic meter suitable for measuring fluid flow, such as liquids or gases, in accordance with embodiments of the invention. Spool piece 100, suitable for placement between sections of a pipeline, has a predetermined size and defines a measurement section. A pair of transducers 120 and 130, and their respective housings 125 and 135, are located along the length of spool piece 100. Transducers 120 and 130 are ultrasonic transceivers, meaning that they both generate and receive ultrasonic signals. "Ultrasonic" in this context refers to acoustic signals, in some embodiments having frequencies above about 20 kilohertz. In some embodiments, the ultrasonic signals may have a frequency of approximately 125 kilohertz (for gas meters), and 1 megahertz (for liquid meters). Regardless of the frequency, these signals may be generated and received by a piezoelectric element in each transducer. To generate an ultrasonic signal, the piezoelectric element is stimulated electrically, and it responds by vibrating. The vibration of the piezoelectric element generates an ultrasonic signal that travels across the spool piece 100 through the fluid to the corresponding transducer of the transducer pair. Upon being struck by an ultrasonic signal, the receiving piezoelectric element vibrates and generates an electrical signal that is detected, digitized, and analyzed by electronics associated with the meter.

A path 110, sometimes referred to as a "chord," exists between transducers 120 and 130 at an angle θ to a centerline 105. The length of "chord" 110 is the distance between the face of transducer 120 to the face of transducer 130. Points 140 and 145 define the locations where acoustic signals generated by transducers 120 and 130 enter and leave fluid flowing through the spool piece 100. The position of transducers 120 and 130 may be defined by the angle θ, by a first length L measured between transducers 120 and 130, a second length X corresponding to the axial distance between points 140 and 145, and a third length D corresponding to the pipe or spool piece diameter. In most cases distances D, X and L are precisely determined during meter fabrication. Further, transducers such as 120 and 130 are usually placed a specific distance from points 140 and 145, respectively, regardless of meter size (i.e. spool piece diameter).

Initially, downstream transducer 120 generates an ultrasonic signal that propagates to and strikes the upstream transducer 130. Some time later, the upstream transducer 130 generates a return ultrasonic signal that propagates to and strikes the downstream transducer 120. Thus, the transducers 120 and 130 play "pitch and catch" with ultrasonic signals 115 along chordal path 110. During operation, this sequence may occur thousands of times per minute for each transducer pair.

A fluid flows in the spool piece 100 in a direction 150 with a velocity profile 152. Velocity vectors 153-158 illustrate that the velocity through spool piece 100 increases toward centerline 105. The transit time of the ultrasonic signal 115 between transducers 120 and 130 depends in part upon whether the ultrasonic signal 115 is traveling upstream or downstream with respect to the fluid flow. A transit time for an ultrasonic signal 115 traveling downstream (i.e. in the same direction as the flow) is less than the transit time when traveling upstream (i.e. against the flow). The upstream and downstream transit times can be used to calculate the average velocity along the chordal path 110, and may also be used to calculate the speed of sound in the fluid flow. Given the cross-sectional measurements of the meter carrying the fluid and the average velocity, the volume of fluid flowing through the spool piece 100 may be calculated.

Figure 2:
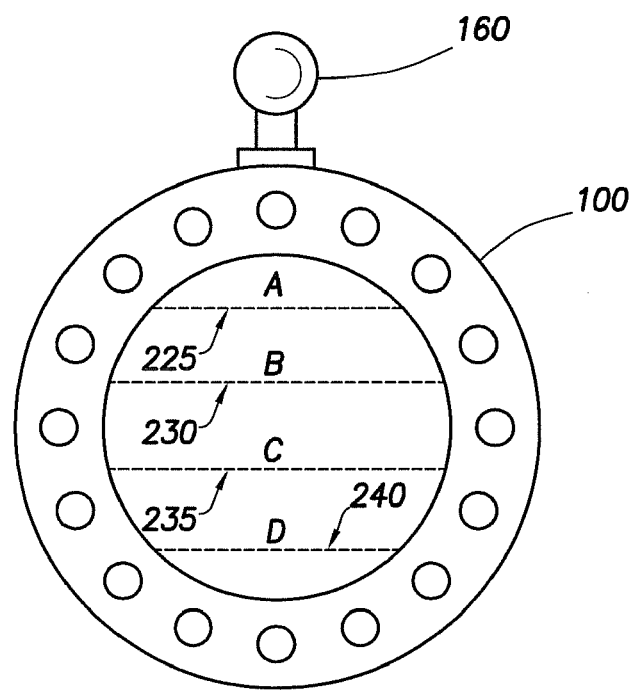
FIG. 2 illustrates an end view of an ultrasonic flow meter in accordance with embodiments of the invention comprising a spool piece and chordal paths A-D.

To more precisely determine the average velocity over the meter cross-section, ultrasonic flow meters comprise a plurality of paths. FIG. 2 illustrates a multi-path ultrasonic flow meter. In these embodiments spool piece 100 comprises a chordal path A 225, a chordal path B 230, a chordal path C 235, and a chordal path D 240 at varying levels through the fluid flow. In alternative embodiments, the multi-path flow meter may comprise a different number of chordal paths. Each chordal path A-D corresponds to two transducers behaving alternately as a transmitter and a receiver. Also shown are control electronics 160, which acquire and process the data from the four chordal paths A-D. Hidden from view in FIG. 2 are the four pairs of transducers that correspond to chordal paths A-D.

The arrangement of the four pairs of transducers may be more easily understood by reference to FIG. 3. Four pairs of transducer ports are mounted on spool piece 100. Each pair of transducer ports corresponds to a single chordal path 110 of FIG. 2. The spool piece 100 has mounted thereon a first pair of transducer ports 125 and 135 as well as associated transducers. Another pair of transducer ports comprising ports 165 and 175 (only partially in view) as well as associated transducers is mounted so that its chordal path loosely forms an "X" with respect to the chordal path 110 of transducer ports 125 and 135. Similarly, transducer ports 185 and 195 are placed parallel to transducer ports 165 and 175 but at a different "level" (i.e. a different radial position in the pipe or meter spool piece). Not explicitly shown in FIG. 3 is a fourth pair of transducers and transducer ports. Taking FIGS. 2 and 3 together, the pairs of transducers are arranged such that the upper two pairs of transducers corresponding to chords A and B form an X, and the lower two pairs of transducers corresponding to chords C and D also form an X. Based on the transit times, the flow velocity of the fluid may be determined at each chord A-D to obtain chordal flow velocities, and the chordal flow velocities may be combined to determine an average flow velocity over the entire pipe or meter spool piece 100.

The chordal flow velocities are based on a batch of transit times received from the four pairs of transducers. The batch of transit times comprise a batch of a difference in transit time ('Δt') between a downstream transit time '$t_1$' and an upstream transit time '$t_2$' generated by substantially the following equation:

$$\Delta t = t_2 - t_1. \tag{1}$$

A batch of 20 values of $\Delta t$ may be used to determine an average value of $\Delta t$. In alternative embodiments, a different number of values of $\Delta t$ may be used.

Based on the average value of $\Delta t$, an average chordal flow velocity may be determined as defined by substantially the following equation:

$$V_i = \frac{L^2}{2X} \frac{\Delta t}{t_2 t_2}, \tag{2}$$

wherein 'i' is indicative of the particular chordal flow velocity being determined (i.e. '$V_A$', '$V_B$', '$V_C$', or '$V_D$' corresponding to chords A-D, respectively), L is the distance between the transducers, and X is the axial distance in the flow. Further, based on the average chordal velocities, an average flow velocity ('$V_{AVG}$') of the flow of fluids through the pipe or meter spool piece 100 may be determined by substantially the following equation:

$$V_{AVG} = W_A V_A + W_B V_B + W_C V_C + W_D V_D, \tag{3}$$

wherein '$W_A$', '$W_B$', '$W_C$', and '$W_D$' are chord-dependent weighting factors.

When combined in various fashions, the chordal velocities provide an indication as to changing conditions such as pipe roughness of the pipe work upstream of the meter or roughness within the meter itself. Specifically, in accordance with some embodiments the asymmetry, cross flow, and profile factor of the flow of fluids through the pipe or meter spool piece 100 are used to determine pipe roughness. Each of these is discussed in turn.

Asymmetry compares the flow in the top half of the pipe or meter ($V_A$, $V_B$) with that in the bottom half of the pipe or meter ($V_C$, $V_D$) and may be generated by substantially the following equation:

$$\text{Asymmetry} = \frac{V_A + V_B}{V_C + V_D}. \tag{4}$$

The cross flow compares the flow in one vertical plane (e.g., a plane defined by chordal path A 225 and chordal path C 235, with corresponding chordal velocities $V_A$ and $V_C$) to the flow in another vertical plane (e.g, a plane defined by chordal path B 230 and chordal path D 240, with corresponding chordal velocities $V_B$ and $V_D$) that may be oriented substantially at a right angle with respect to one another and may be generated by substantially the following equation:

$$\text{Cross Flow} = \frac{V_A + V_C}{V_B + V_D}. \tag{5}$$

Profile factor compares the flow near the center of the pipe or meter ($V_B$, $V_C$) to the flow near the pipe or meter wall ($V_A$, $V_D$) and may be generated by substantially the following equation:

$$\text{Profile Factor} = \frac{V_B + V_C}{V_A + V_D}. \tag{6}$$

The profile factor also provides an indication as to swirl of the flow due to both the varying radial positions and planes of the chordal paths A-D. Under optimum operating conditions, the asymmetry value should be about unity, the cross flow value should be about unity, and the profile factor value should be about 1.17.

Figure 4:
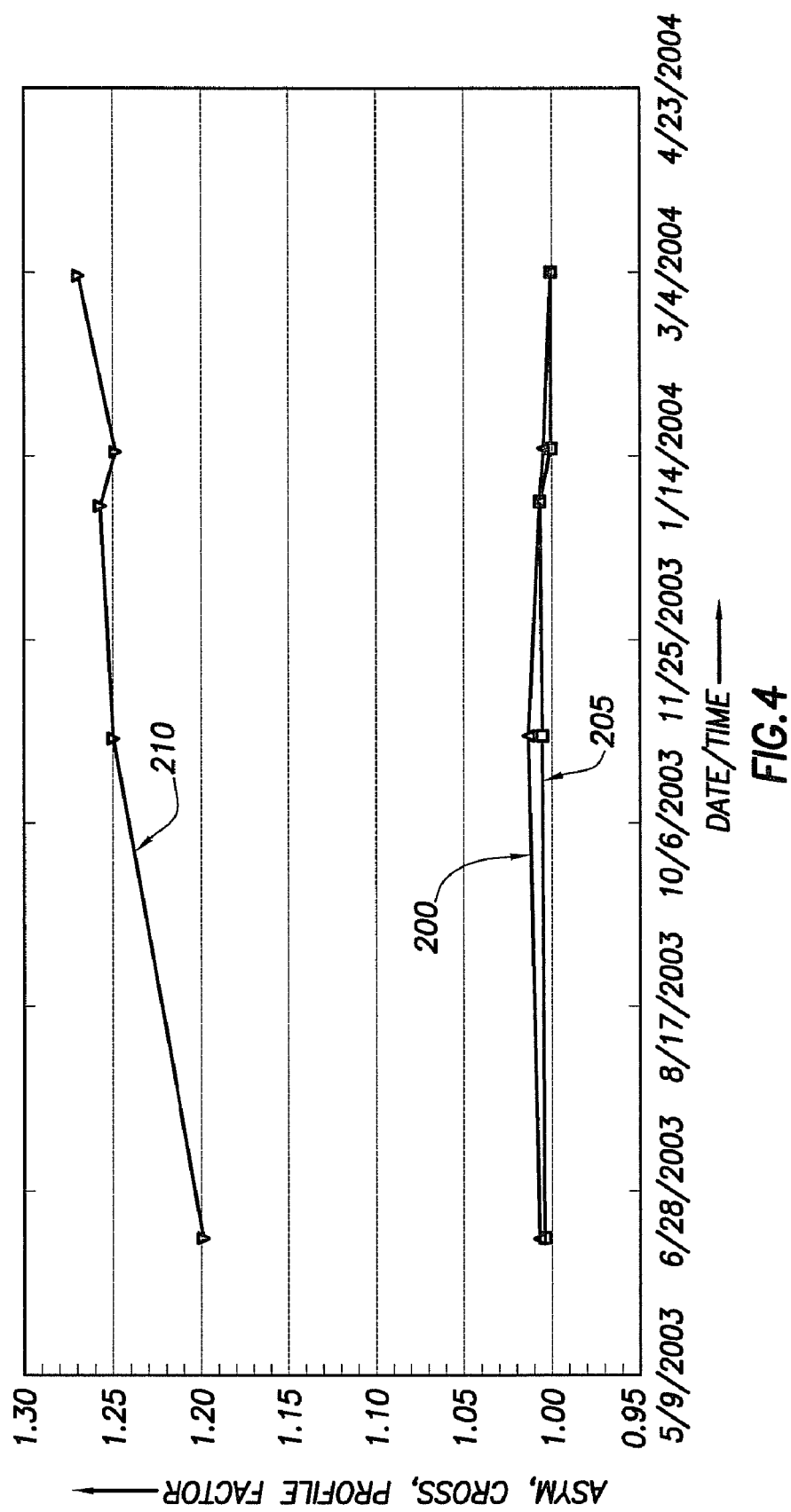
FIG. 4 illustrates a trend of diagnostic data with time in accordance with embodiments of the invention comprising asymmetry, cross flow, and profile factor data.

Referring now to the illustration of FIG. 4, the asymmetry 200, cross flow 205, and profile factor 210 are plotted as a function of time. Time is plotted along the x-axis, and the asymmetry 200, cross flow 205, and profile factor 210 are plotted along the y-axis. The trend of this diagnostic data with time illustrates a substantially constant value of about unity (the optimum operating value) for both the asymmetry 200 and the cross flow 205 and a substantially increasing value away from about 1.17 (the optimum operating value) for the profile factor 210 of the flow of fluids through the pipe or meter. This trend in the data indicates that flow remains symmetrical and there is substantially no cross flow, while the flow velocities near the center of the pipe or meter (chordal paths B 230 and C 235) are increasing as compared to flow velocities near the pipe or meter wall (chordal paths A 225 and D 240).

The diagnostic data illustrated in FIG. 4 is illustrative of an indication as to changing conditions such as pipe or meter roughness. More specifically, the trend of the data as shown in FIG. 4 provides an indication of an increase in pipe roughness of the upstream pipe work or an increase in roughness of the meter spool piece 100.

Returning to FIG. 1, the velocity profile 152 is established by the pipe condition upstream of the meter or upstream of the transducers. For example, if the upstream pipe and fittings are fixed, one would not expect a change in the velocity profile 152. However, there are conditions under which the velocity profile 152 may change such as: an upstream flow control valve being adjusted; an upstream branching flow of varying proportion to the metered flow; a flow conditioner trapping debris; or erosion, corrosion, or deposition changing the upstream pipe or meter roughness.

Figure 5:
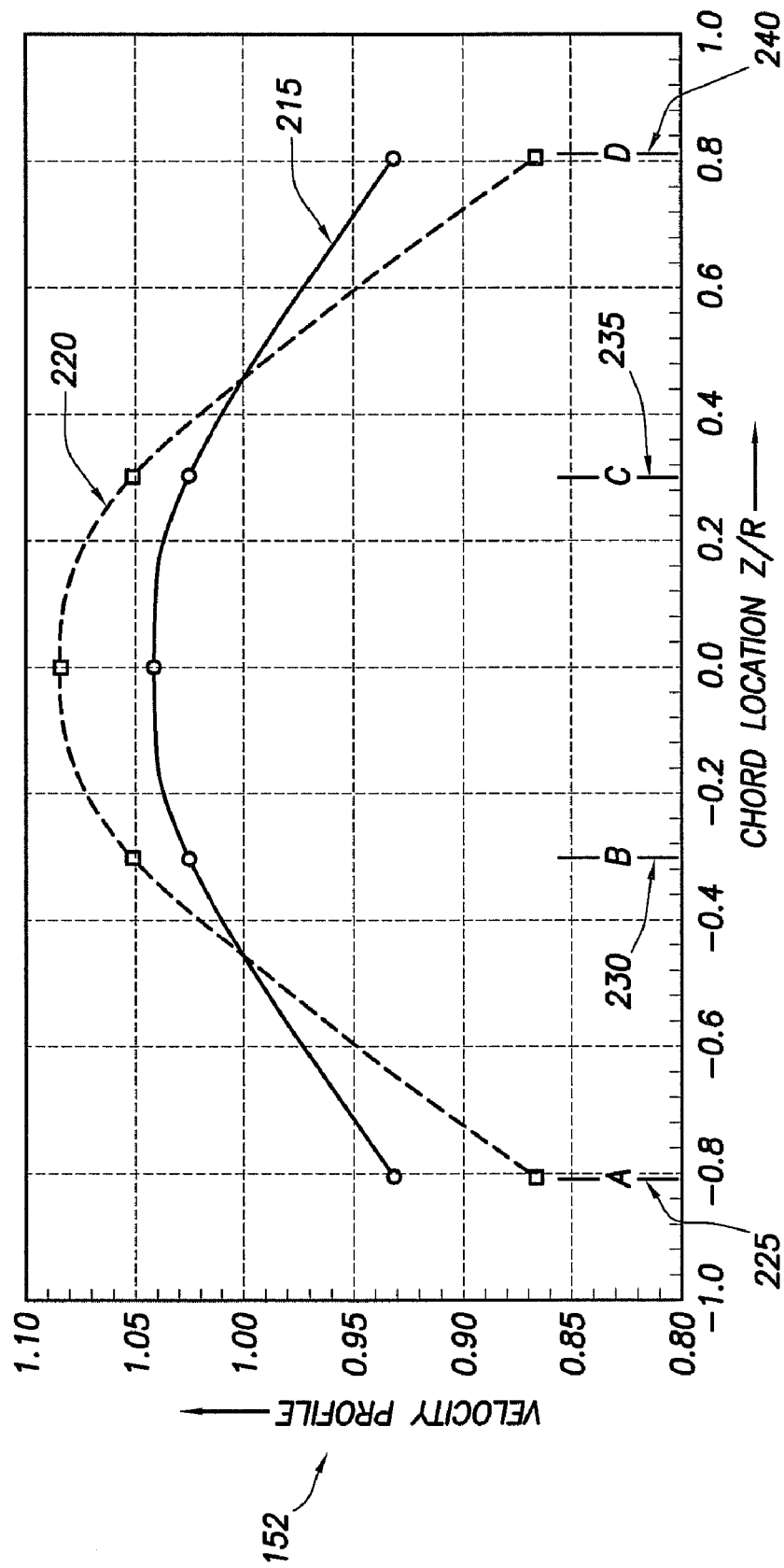
FIG. 5 illustrates diagnostic data in accordance with embodiments of the invention comprising velocity profile data for smooth and rough pipelines.

The change in velocity profile 152 due to one of the aforementioned factors may be more easily understood with reference to FIG. 5. FIG. 5 illustrates the velocity profile 152 as a function of the location of the chords A-D for both smooth 215 (solid curve) and rough 220 (dashed curve) upstream conditions. The chord location is plotted along the x-axis with the position corresponding to chordal path A 225, chordal path B 230, chordal path C 235, and chordal path D 240 also noted. The velocity profile 152 (which is a dimensionless number) is plotted along the y-axis wherein the velocity profile 152 is defined by substantially the following equation:

$$\text{Velocity Profile} = \frac{V_{CHORD}}{V_{AVG}}, \tag{7}$$

wherein '$V_{CHORD}$' is the chordal flow velocity of one of the chords A-D and $V_{AVG}$ is the average velocity of the flow of fluids in the spool piece as defined above.

For rough upstream conditions (curve 220) the velocity near a pipe or meter wall ($V_A$, $V_D$ based on chordal path A 225 and chordal path D 240) is reduced because of increased resistance due to the pipe or meter roughness. Concurrently, the velocity near the center of the pipe or meter ($V_B$, $V_C$ based on chordal path B 230 and chordal path C 235) is increased because the same mass flow will travel through the flow meter due to the principle of continuity. Thus, the velocity profile 152 takes on a more acute shape for the case of rough upstream conditions (again, curve 220) as compared to the case of smooth upstream conditions (curve 215).

Figure 6:
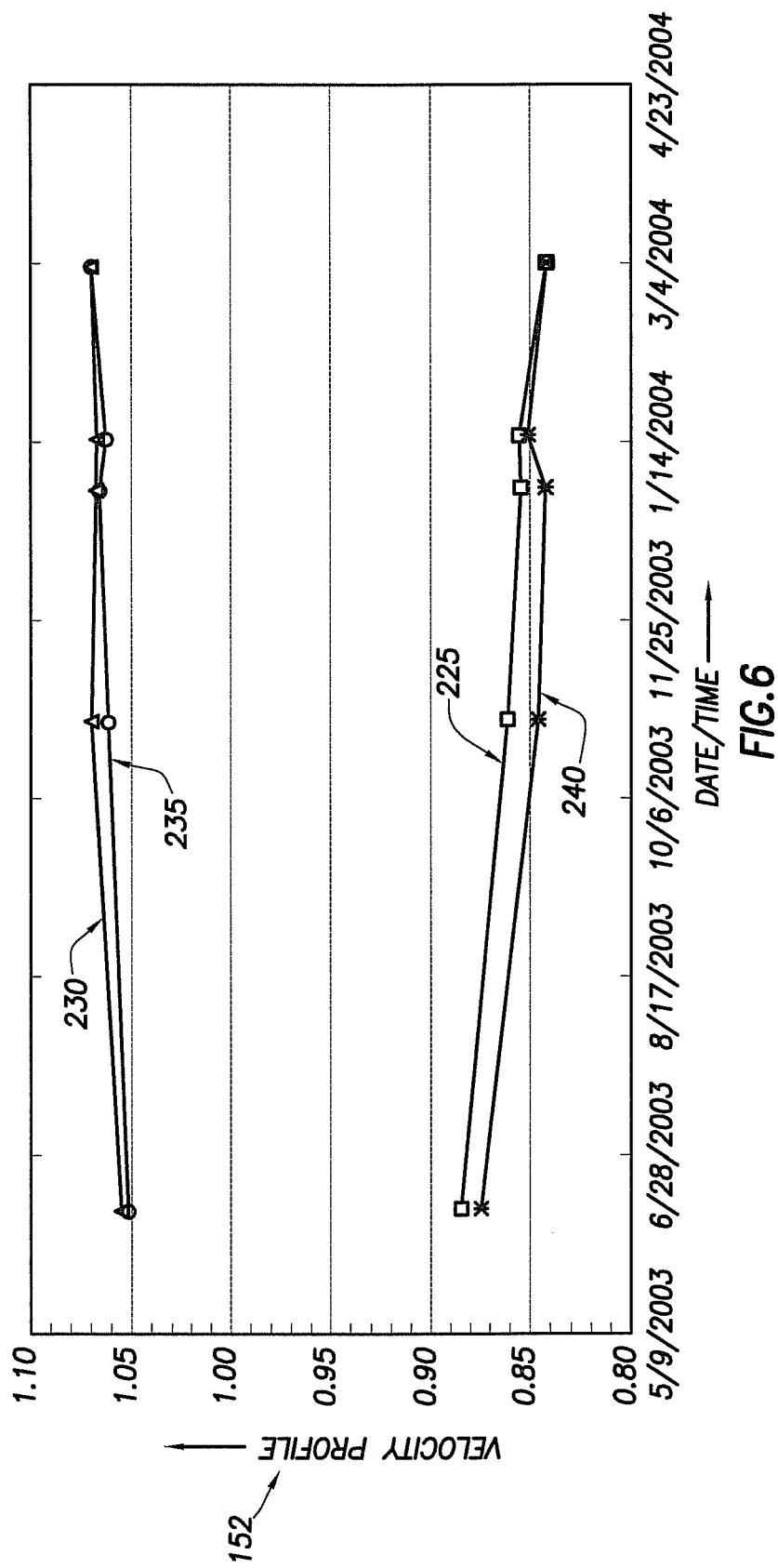
FIG. 6 illustrates a trend of diagnostic data with time in accordance with embodiments of the invention comprising velocity profile data.

FIG. 6 illustrates the velocity profile 152 as a function of time for the varying locations of the chords A-D. Time is plotted along the x-axis, and the velocity profile 152 corresponding to chordal paths A-D is plotted along the y-axis. As similarly illustrated in FIG. 5, FIG. 6 shows a decrease in velocity near the pipe or meter wall (velocity profile 152 corresponding to chordal path A 225 and chordal path D 240) and a concurrent increase in velocity near the center of the pipe or meter (velocity profile 152 corresponding to chordal path B 230 and chordal path C 235). Moreover, FIG. 6 shows this change as a function of time. Thus, the velocity profile 152 component of the diagnostic data as illustrated in FIG. 6 provides an additional indicator as to the changing conditions of the pipe or meter over time.

Another component of the diagnostic data, a turbulence value, may be generated based on the batch of $\Delta t$ values. Taking the average $\Delta t$ and a standard deviation of $\Delta t$ ('$\sigma\Delta t$'), turbulence (i.e. velocity fluctuation) may be defined substantially by the following equation:

$$\text{Turbulence} = \frac{\sigma\Delta t}{\Delta t} * 100\%. \quad (8)$$

The turbulence may be interpreted as a measure of the velocity fluctuation for each chordal path A-D. Under optimal operating conditions, the turbulence is about 1-2% for inner chordal paths B 230 and C 235 and about 3-4% for outer chordal paths A 225 and D 240.

Figure 7:
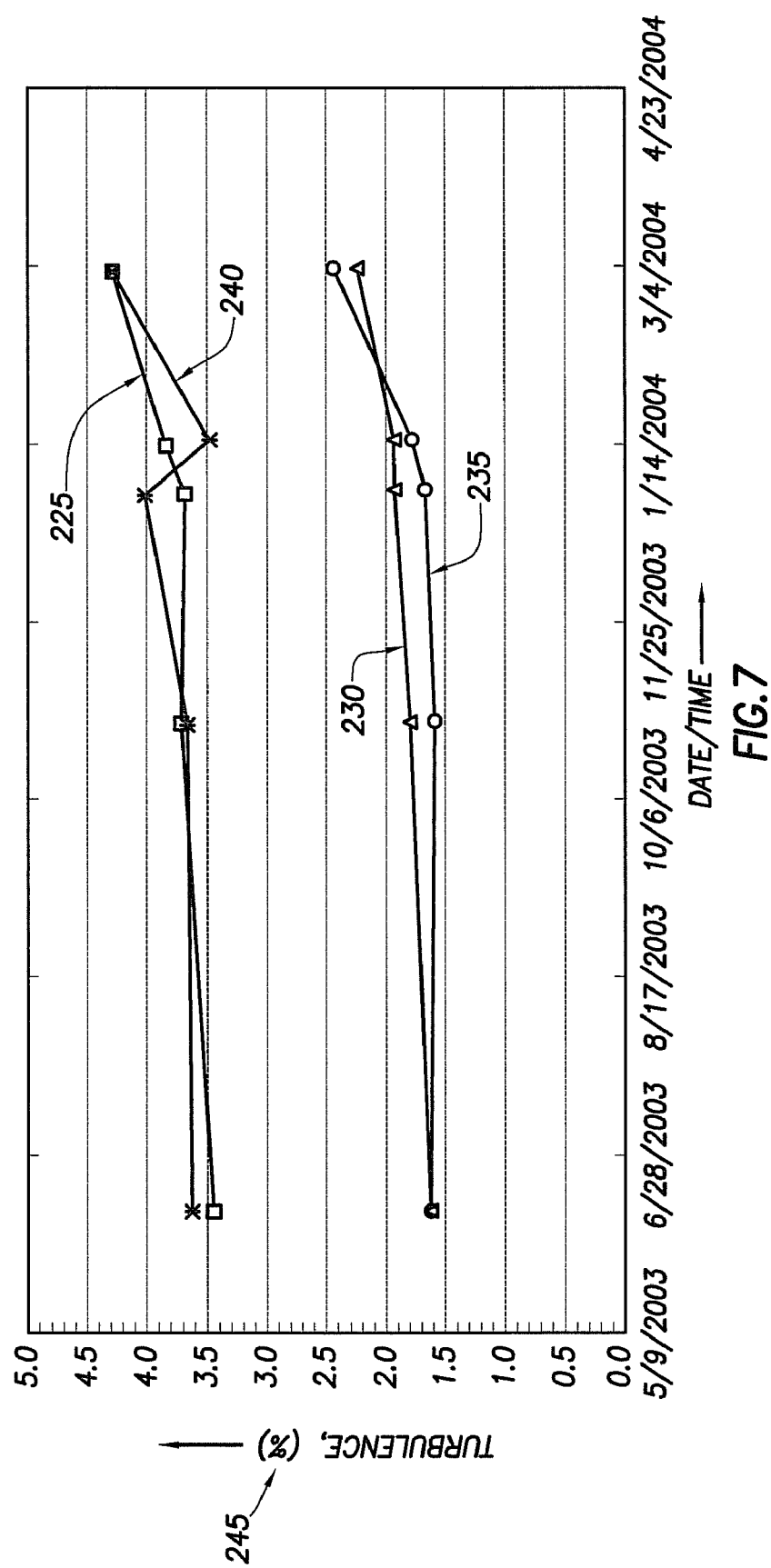
FIG. 7 illustrates a trend of diagnostic data with time in accordance with embodiments of the invention comprising turbulence data.

FIG. 7 is an illustration of turbulence 245 as a function of time. Time is plotted along the x-axis, and the percentage of turbulence 245 is plotted along the y-axis. As shown in FIG. 7, the initial percentage of turbulence 245 is higher for chordal paths A 225 and D 240 as compared to the turbulence 245 for chordal paths B 230 and C 235. With increasing time, the turbulence 245 along all chordal paths increases. This result is indicative of an increased upstream pipe or meter roughness as such factors may cause increased turbulence 245 as well as increases in friction loss and shear stress. Thus, the turbulence data also provides an additional indicator as to the changing conditions of the upstream pipe work.

FIG. 8 illustrates a flow diagram for an algorithm used for determining pipe roughness in accordance with embodiments of the invention. The process starts (block 300) and proceeds to the determination of diagnostic data based on ultrasonic signals (block 302) transmitted between pairs of transducers. In some embodiments, the diagnostic data comprises the asymmetry 200, cross flow 205, and profile factor 210 of the flow of fluids through the pipe or meter spool piece 100. Other embodiments may consider velocity profile 152 and turbulence data 245 as well. The process then proceeds to the trending of the diagnostic data with time (block 304). The trending may be performed over a period of time as determined by a user as being adequate, and in some embodiments may be on the order of months or years. After predetermined period of time allocated for trending of the diagnostic data, the process proceeds to the determination of changes in the roughness of the pipe or meter based on the trend of the data (block 306). In some embodiments the determination of pipe roughness is made based on the subset of diagnostic data comprising the asymmetry 200, cross flow 205, and profile factor 210. In other embodiments the determination of pipe or meter roughness may be supported as well by the velocity profile 152 and turbulence data 245. After determination of the pipe and meter condition, the process then proceeds to the determination of additional diagnostic data based on ultrasonic signals 115 (block 302).

From the description provided herein, those skilled in the art are readily able to combine the methods as described to create software that when combined with appropriate general purpose or special purpose computer hardware may be used to create a computer system and/or computer subcomponents embodying the invention, to create a computer system and/or computer subcomponents for carrying out the method of the invention, and/or to create a computer-readable media for storing a software program to implement the method aspects of the invention.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An ultrasonic meter comprising:
a spool piece that couples within a flow of fluids; and
a first transducer pair mechanically mounted to the spool piece and acoustically coupled to the flow of fluids, the first transducer pair comprising an upstream transducer and a downstream transducer in operational relationship to the upstream transducer and defining a first chord there between;
the ultrasonic meter is configured to determine diagnostic data based on acoustic signals transmitted between the first transducer pair, the diagnostic data comprising: asymmetry of the flow of fluids in the spool piece; cross flow of the flow of fluids in the spool piece; and profile factor of the flow of fluids in the spool piece; and
the ultrasonic meter is configured to determine that changes in the roughness of a pipe mechanically coupled to the ultrasonic meter have occurred when a trend of the diagnostic data with respect to time comprises a substantially constant value of about unity for both the asymmetry and the cross flow and a substantially changing value for the profile factor.

2. The ultrasonic meter as defined in claim 1 wherein the diagnostic data further comprises a velocity profile of the flow of fluids in the spool piece, and the ultrasonic meter is further configured to determine that changes in the roughness of the pipe have occurred based on the velocity profile.

3. The ultrasonic meter as defined in claim 1 wherein the diagnostic data further comprises a value indicative of turbulence of the flow of fluids in the spool piece, and the ultrasonic meter is further configured to determine that changes in the roughness of the pipe have occurred based on the value indicative of turbulence.

4. The ultrasonic meter as defined in claim 3 wherein the value indicative of turbulence of the flow of fluids in the spool piece is generated by substantially the following equation:

$$\text{Turbulence} = \frac{\sigma \Delta t}{\Delta t} * 100\%,$$

wherein '$\Delta t$' is a difference between a transit time '$t_1$' and a transit time '$t_2$' generated by substantially the following equation:

$$\Delta t = t_2 - t_1, \text{ and}$$

wherein '$\sigma \Delta t$' is a standard deviation of '$\Delta t$'.

5. The ultrasonic meter as defined in claim 1 further comprising:
a second transducer pair mechanically mounted to the spool piece and acoustically coupled to the flow of fluids, the second transducer pair comprising an upstream transducer and a downstream transducer in operational relationship to the upstream transducer and defining a second chord there between;
a third transducer pair mechanically mounted to the spool piece and acoustically coupled to the flow of fluids, the third transducer pair comprising an upstream transducer and a downstream transducer in operational relationship to the upstream transducer and defining a third chord there between; and
a fourth transducer pair mechanically mounted to the spool piece and acoustically coupled to the flow of fluids, the fourth transducer pair comprising an upstream transducer and a downstream transducer in operational relationship to the upstream transducer and defining a fourth chord there between;
the ultrasonic meter is configured to determine diagnostic data based on acoustic signals transmitted between each of the second, third, and fourth transducer pairs.

6. The ultrasonic meter as defined in claim 5 wherein each of the first, second, third, and fourth chords are defined at varying radial positions within the spool piece.

7. The ultrasonic meter as defined in claim 6 wherein the diagnostic data further comprises a velocity profile of the flow of fluids in the spool piece based on the varying radial positions of the chords, and the ultrasonic meter is configured to determine that changes in the roughness of the pipe have occurred based on the velocity profile.

8. The ultrasonic meter as defined in claim 5 further configured to determine a velocity '$V_A$' associated with the first transducer pair, a velocity '$V_B$' associated with the second transducer pair, a velocity '$V_C$' associated with the third transducer pair, and a velocity '$V_D$' associated with the fourth transducer pair.

9. The ultrasonic meter as defined in claim 8 wherein the asymmetry of the flow of fluids in the spool piece is generated by substantially the following equation:

$$\text{Asymmetry} = \frac{V_A + V_B}{V_C + V_D}.$$

10. The ultrasonic meter as defined in claim 8 wherein the cross flow of the flow of fluids in the spool piece is generated by substantially the following equation:

$$\text{Cross Flow} = \frac{V_A + V_C}{V_B + V_D}.$$

11. The ultrasonic meter as defined in claim 8 wherein the profile factor of the flow of fluids in the spool piece is generated by substantially the following equation:

$$\text{Profile Factor} = \frac{V_B + V_C}{V_A + V_D}.$$

12. The ultrasonic meter as defined in claim 8 wherein a velocity profile of the flow of fluids in the spool piece is generated by substantially the following equation:

$$\text{Velocity Profile} = \frac{V_{CHORD}}{V_{AVG}},$$

wherein '$V_{CHORD}$' comprises '$V_A$', '$V_B$', '$V_C$', and '$V_D$', and wherein '$V_{AVG}$' is an average velocity of the flow of fluids in the spool piece and is generated by substantially the following equation:

$$V_{AVG} = W_A V_A + W_B V_B + W_C V_C + W_D V_D, \text{ and}$$

wherein '$W_A$', '$W_B$', '$W_C$', and '$W_D$' are chord-dependent weighting factors.

13. The system as defined in claim 1 further comprising the ultrasonic meter is configured to use the diagnostic data for condition based monitoring of the ultrasonic meter.

14. A method comprising:
transmitting acoustic signals between a first transducer pair of an ultrasonic meter;
determining diagnostic data based on the acoustic signals, the diagnostic data comprising: asymmetry of a flow of fluids that couples within a spool piece; cross flow of the flow of fluids in the spool piece; and profile factor of the flow of fluids in the spool piece;
trending the diagnostic data with time; and
determining that changes in the roughness of a pipe have occurred when the trend comprises a substantially constant value of about unity for both the asymmetry and the cross flow and a substantially changing value for the profile factor.

15. The method as defined in claim 14 further comprising:
determining the diagnostic data further comprises a velocity profile of the flow of fluids in the spool piece; and
changes in the roughness of the pipe have occurred further comprises determining based on the velocity profile.

16. The method as defined in claim 14 further comprising:
determining the diagnostic data further comprises a turbulence of the flow of fluids in the spool piece; and
determining that changes in the roughness of the pipe have occurred further comprises determining based on the turbulence.

17. The method as defined in claim 14 wherein determining diagnostic data further comprises determining diagnostic data based on acoustic signals transmitted between each of a second, third, and fourth transducer pair.

18. The method as defined in claim 14 further comprising using the diagnostic data for condition based monitoring of an ultrasonic meter.

19. A computer-readable media comprising a plurality of instructions that, when executed by a processor, cause the processor to:
trend of diagnostic data with time, the diagnostic data is based on acoustic signals transmitted between a first transducer pair and comprises: asymmetry of a flow of fluids that couples within a spool piece; cross flow of the flow of fluids in the spool piece; and profile factor of the flow of fluids in the spool piece; and determine that changes in the roughness of a pipe have occurred when the trend comprises a substantially constant value of about unity for both the asymmetry and the cross flow and a substantially changing value for the profile factor.

20. The computer-readable media as defined in claim 19 wherein the plurality of instructions further cause the processor to perform condition based monitoring of an ultrasonic meter.

* * * * *